US009829455B2

(12) United States Patent
Watanabe et al.

(10) Patent No.: US 9,829,455 B2
(45) Date of Patent: Nov. 28, 2017

(54) GAS DETECTOR

(71) Applicant: NGK Spark Plug Co., LTD., Nagoya (JP)

(72) Inventors: Masaya Watanabe, Komaki (JP); Shoji Kitanoya, Kasugai (JP); Daisuke Ichikawa, Kani (JP); Masahiro Yamashita, Komaki (JP); Yusuke Matsukura, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 111 days.

(21) Appl. No.: 14/555,010

(22) Filed: Nov. 26, 2014

(65) Prior Publication Data

US 2015/0153294 A1    Jun. 4, 2015

(30) Foreign Application Priority Data

Nov. 29, 2013 (JP) .................................. 2013-247812
Aug. 19, 2014 (JP) .................................. 2014-166941
Nov.  4, 2014 (JP) .................................. 2014-224762

(51) Int. Cl.
*G01N 27/16* (2006.01)
*G01N 25/18* (2006.01)
*G01N 27/18* (2006.01)

(52) U.S. Cl.
CPC ............. *G01N 27/16* (2013.01); *G01N 25/18* (2013.01); *G01N 27/18* (2013.01)

(58) Field of Classification Search
None
See application file for complete search history.

(56) References Cited

U.S. PATENT DOCUMENTS

| | | | | |
|---|---|---|---|---|
| 5,652,443 A | * | 7/1997 | Kasai | G01N 27/18 257/252 |
| 2012/0204623 A1 | * | 8/2012 | Matsuno | G01N 25/18 73/25.03 |

FOREIGN PATENT DOCUMENTS

| | | |
|---|---|---|
| JP | 2005-156364 A | 6/2005 |
| JP | 2005-164570 A | 6/2005 |
| JP | 2010-96727 A | 4/2010 |

OTHER PUBLICATIONS

European Search Report dated Mar. 31, 2015 for the corresponding European Application No. 14195207.7.

* cited by examiner

*Primary Examiner* — Paul West
*Assistant Examiner* — Mark A Shabman
(74) *Attorney, Agent, or Firm* — Leason Ellis LLP

(57) ABSTRACT

A gas detector includes a gas detection element having a protection layer formed of an oxide film mainly containing tantalum oxide ($Ta_2O_5$). Since the protection layer has excellent condensed-water resistance, even when water droplets adhere thereto, the morphology thereof does not change from dense to porous. Thus, since a change in property of the protection layer, which would otherwise be caused by adhesion of water droplets, can be reduced in the gas detector, even when water droplets adhere to the outermost surface layer of the gas detection element, impurities can be prevented from entering the protection layer (the outermost surface layer), whereby a change in thermal capacity of the gas detection element can be reduced. Thus, the gas detection element of the gas detector has excellent alkali resistance and condensed-water resistance.

14 Claims, 10 Drawing Sheets

GAS DETECTOR

This application claims the benefit of Japanese Patent Applications No. 2013-247812, filed Nov. 29, 2013, No. 2014-166941, filed Aug. 19, 2013 and No. 2014-224762, filed Nov. 4, 2014, which are incorporated by reference in their entities herein.

FIELD OF THE INVENTION

The present invention relates to a gas detector for use in, for example, measuring the concentration of a flammable gas or detecting leakage of a flammable gas.

BACKGROUND OF THE INVENTION

In view of implementation of space saving and low power consumption, demand exists to further reduce the size of gas detectors for measuring the concentration of a flammable gas or detecting leakage of a flammable gas. In recent years, gas detection elements with greatly reduced sizes have been developed by use of MEMS (Micro-Electro-Mechanical System) technology (also called the micromachining technique). A gas detection element formed by use of MEMS technology is configured such that a plurality of thin films are formed in layers on a semiconductor substrate (e.g., a silicon substrate).

Examples of such a gas detection element include a thermal-conductivity-type gas detection element and a catalytic-combustion-type gas detection element. The thermal-conductivity-type gas detection element has a heat-generating resistor and utilizes the phenomenon that, when the heat-generating resistor is energized and generates heat, heat is conducted to a flammable gas. Specifically, in the case of controlling the gas detection element at a constant temperature, conduction of heat causes a change in temperature of the heat-generating resistor and thus a change in resistance of the heat-generating resistor. On the basis of the amount of the change, a gas-to-be-detected is detected. The catalytic-combustion-type gas detection element has a heat-generating resistor and a catalyst, which causes combustion of a flammable gas by means of heat of the heat-generating resistor. The catalytic-combustion-type gas detection element utilizes the phenomenon that, when the heat-generating resistor is energized, the catalyst causes combustion of a flammable gas. Specifically, the heat-generating resistor changes in temperature and resistance according to heat of combustion of a flammable gas. On the basis of the amount of the change, a flammable gas is detected.

In both the thermal-conductivity-type gas detection element and the catalytic-combustion-type gas detection element, the resistance of the heat-generating resistor varies with the type or concentration of a flammable gas. Thus, a gas detector having such a gas detection element can detect a flammable gas on the basis of the resistance of the heat-generating resistor.

Such a gas detection element is configured as follows: an insulation layer is disposed on a semiconductor substrate, and a heat-generating resistor is disposed in the insulation layer. Preferably, the outermost surface (specifically, a surface which comes into contact with a gaseous atmosphere that contains a flammable gas) of the insulation layer has excellent corrosion resistance and excellent stability. A gas detection element fabricated by use of MEMS technology may be configured such that the outermost surface of the insulation layer is of silicon nitride (refer to Japanese Patent Application Laid-Open (kokai) No. 2005-156364). However, silicon nitride or a like material may tend to be eroded by an alkali substance adhering thereto. Thus, improvement in durability against alkali is desired.

In order to prevent erosion caused by adhesion of an alkali substance, provision of a protection layer resistant to alkali (hereinafter, referred to as the alkali-resistant protection layer) on the surface formed of silicon nitride or the like is conceived (refer to, for example, Japanese Patent Application Laid-Open (kokai) No. 2005-164570). According to Japanese Patent Application Laid-Open (kokai) No. 2005-164570, the alkali-resistant protection layer is formed by a so-called spin coating process. Specifically, alumina sol is applied to the surface in a layered manner, followed by firing. By this process, an alumina layer (i.e., an alkali-resistant protection layer) is formed.

There has also been proposed a configuration in which the outermost surface layer of a gas detection element is formed of an oxide film exhibiting high alkali resistance (Japanese Patent Application Laid-Open (kokai) No. 2010-096727). This configuration can prevent erosion of the gas detection element even when an alkaline substance adheres to the surface of the element.

The oxide film formed on the gas detection element described in Japanese Patent Application Laid-Open (kokai) No. 2010-096727 has gas impermeability (i.e., a dense structure). Thus, impurities (e.g., an organic silicon compound) can be prevented from entering the oxide film.

That is, this configuration can prevent impurities from entering the outermost surface layer of the gas detection element, to thereby reduce a change in thermal capacity. Accordingly, the output of the gas detection element is stabilized and becomes accurate, whereby high detection accuracy can be achieved.

Problems to be Solved by the Invention

However, when the aforementioned conventional gas detection element is used in a high-humidity environment where dew condensation occurs, moisture may impair the gas detection accuracy of the gas detection element.

When, for example, water droplets resulting from dew condensation adhere to the oxide film formed on the aforementioned conventional gas detection element, the oxide film may be eroded by the water droplets, and the morphology of the oxide film may change from dense to porous. Such a change in property of the oxide film may cause an error in the output of the gas detection element.

An object of the present invention is to provide a gas detector which is used for, for example, measuring the concentration of a flammable gas or detecting leakage of a flammable gas, and which includes a gas detection element having excellent alkali resistance and resistance to water droplets resulting from dew condensation (hereinafter referred to as "condensed-water resistance").

SUMMARY OF THE INVENTION

Means for Solving the Problems (1) In one aspect of the present invention, there is provided a gas detector comprising a thermal-conductivity-type gas detection element and control means. The gas detection element is configured such that at least a heat-generating resistor and an insulation layer are laminated on a semiconductor substrate, and the insulation layer covers the heat-generating resistor. The control means controls energization of the heat-generating resistor and detects a gas-to-be-detected on the basis of resistance of the energized heat-generating resistor.

The gas detection element has a gas impermeable oxide film laminated on a surface of the insulation layer in such a manner as to cover the insulation layer. The oxide film contains at least one of Ta, Nb, and Hf, and forms an outermost surface layer which comes into contact with a gaseous atmosphere containing the gas-to-be-detected.

As used herein, the term "detect" refers not only to determine whether or not a gas-to-be-detected is present, but also to measure the concentration of the gas-to-be-detected. The expression "an oxide film has gas impermeability" refers to the oxide film being formed densely to such an extent as not to allow a gas to pass therethrough.

In the gas detector, the outermost surface layer of the gas detection element is formed of an oxide film containing at least one of Ta, Nb, and Hf. Therefore, even when water droplets adhere to the surface of the gas detection element, erosion of the oxide film by the water droplets can be prevented. That is, since the oxide film has excellent condensed-water resistance, even when water droplets adhere thereto, the morphology thereof does not change from dense to porous.

Thus, since a change in property of the oxide film, which would otherwise be caused by adhesion of water droplets, can be reduced in the gas detector, even when water droplets adhere to the outermost surface layer of the gas detection element, impurities can be prevented from entering the oxide film (the outermost surface layer), whereby a change in thermal capacity of the gas detection element can be reduced.

Needless to say, the oxide film, which is formed of an oxide material, exhibits excellent alkali resistance. Therefore, for example, even when an alkaline substance adheres to the surface of the gas detection element, erosion by the alkaline substance can be prevented.

Furthermore, the oxide film, which has gas impermeability (a dense structure), can prevent entry thereinto of impurities (e.g., an organic silicon compound) contained in an environmental atmosphere containing a gas-to-be-detected. For example, when the oxide film has a porous structure (i.e., gas permeability), impurities are likely to adhere to the oxide film through entry into pores. However, the present invention is free from such adhesion; i.e., the configuration of the invention can prevent impurities from entering the outermost surface layer of the gas detection element, to thereby reduce a change in thermal capacity.

As described above, the gas detection element of the gas detector of the present invention has excellent alkali resistance and condensed-water resistance. Thus, according to the gas detector of the present invention, the output of the gas detection element is stabilized and becomes accurate, whereby high gas detection accuracy can be achieved.

(2) In the gas detector according to another aspect of the present invention, the oxide film may mainly contain tantalum oxide.

That is, the oxide film containing at least one of Ta, Nb, and Hf is, for example, an oxide film mainly containing tantalum oxide ($Ta_2O_5$).

The oxide film mainly containing tantalum oxide ($Ta_2O_5$) enables the gas detection element of the gas detector to have excellent alkali resistance and condensed-water resistance.

As used herein, the expression "oxide film mainly containing tantalum oxide" refers to the oxide film containing tantalum oxide in an amount of 50 vol % or more.

(3) In the gas detector according to still another aspect of the present invention, the surface of the insulation layer may be formed of silicon nitride.

Since silicon nitride has excellent corrosion resistance and stability, the durability of the gas detection element can be enhanced in combination with excellent alkali resistance and condensed-water resistance being attained through provision of the oxide film.

(4) In the gas detector according to yet another aspect of the present invention, the oxide film may have a thickness equal to or greater than one-fiftieth of a thickness of the heat-generating resistor as measured in a direction perpendicular to front and back surfaces of the semiconductor substrate.

When the thickness of the oxide film is determined to be such a level, generation of holes (spots or pores) can be prevented in the oxide film.

(5) In the gas detector according to yet another aspect of the present invention, the oxide film may have a thickness of 5 to 200 nm.

When the lower limit of the thickness of the oxide film is determined as described above, generation of holes (spots or pores) can be prevented in the oxide film.

Meanwhile, when the upper limit of the thickness of the oxide film is determined as described above, an excessive increase in thickness of the oxide film can be prevented, to thereby avoid a problem of poor flexibility of the oxide film against, for example, thermal expansion and contraction.

(6) In the gas detector according to yet another aspect of the present invention, the thickness of the oxide film may be a distance between the surface of the insulation layer and a surface of the oxide film which comes into contact with the gaseous atmosphere.

This means the following: as viewed at any point on the surface of the insulation layer, the thickness of the oxide film conforms to the aforementioned specific thickness range; in other words, the surface of the insulation layer has irregularities to a certain extent stemming from the existence of the heat-generating resistor within the insulation layer, and the oxide film is formed in such a manner as to have a specific thickness as measured along the irregular surface profile.

Thus, the distance from an edge of the irregular surface profile of the insulation layer to the surface of the oxide film reliably falls within the required range, thereby preventing variation in the effect of provision of the oxide film, which could otherwise result from the irregularities.

(7) In the gas detector according to yet another aspect of the present invention, the oxide film may be formed through a sputtering process.

According to the sputtering process, ions are caused to impinge on a desired material so as to eject particles of the material, and the ejected particles adhere to a target, thereby forming a desired thin film on the target. The sputtering process can form a denser film.

(8) In the gas detector according to yet another aspect of the present invention, the gas detection element may be a thermal-conductivity-type gas detection element or a catalytic-combustion-type gas detection element.

When a thermal-conductivity-type gas detection element or a catalytic-combustion-type gas detection element is provided with the aforementioned oxide film, the resultant gas detection element exhibits excellent alkali resistance and condensed-water resistance. The gas detector including such a gas detection element exhibits high gas detection accuracy, since the output of the gas detection element is stabilized and becomes accurate.

In particular, the thermal-conductivity-type gas detection element is conceived to take greater advantage of the effect of provision of the oxide film. That is, a gas-to-be-detected has very low thermal conductivity. Also, in order to detect a gas-to-be-detected having a low concentration on the order of ppm (parts per million), the output of the gas detection element must be amplified. Thus, when the output of the gas detection element involves an error, the error is also enlarged. Therefore, a smaller error is more preferred.

The present invention is advantageous in that, since a change in property of the oxide film, which would otherwise be caused by water droplets, can be prevented, a change in thermal capacity, which may be due to entry of impurities, can also be reduced, resulting in a reduction in error.

(9) In the gas detector according to yet another aspect of the present invention, the gas-to-be-detected may be hydrogen gas.

The gas detector of the present invention configured to detect, for example, hydrogen gas is suitable for practical use.

(10) The gas detector according to yet another aspect of the present invention may be configured such that at least the gas detection element is disposed at a specific position on a fuel cell system for generating electricity from hydrogen and oxygen, and is adapted to detect hydrogen gas used in the fuel cell system.

The gas detector of the present invention configured to detect, for example, hydrogen gas in a fuel cell system is suitable for practical use.

Effects of the Invention

The present invention realizes a gas detector including a gas detection element having excellent alkali resistance and condensed-water resistance. Thus, in the gas detector of the present invention, the output of the gas detection element is stabilized and becomes accurate, whereby high gas detection accuracy can be achieved.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Embodiments of the present invention will next be described with reference to the drawings.

The embodiments will be described by taking, as an example, a gas detector for detecting hydrogen gas. More specifically, the embodiments will be described by taking, as an example, a gas detector used for detecting leakage of hydrogen gas in a fuel cell system for generating electricity from hydrogen and oxygen.

1. First Embodiment

[1-1. Entire Configuration]

Figure 1:
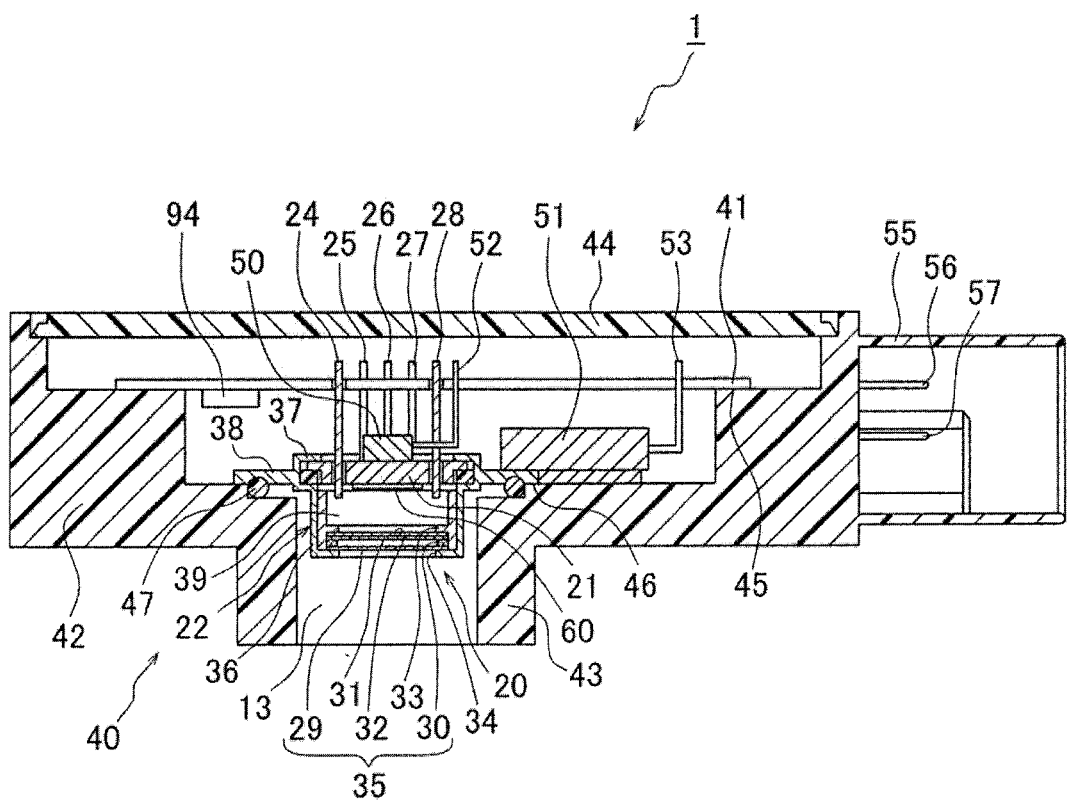
FIG. 1 is a longitudinal sectional view of a gas detector 1 according to an embodiment.

FIG. 1 is a longitudinal sectional view of a gas detector 1 to which the present invention is applied. The gas detector 1 is used, for example, to detect leakage of hydrogen gas used in a fuel cell system for generating electricity from hydrogen and oxygen.

The gas detector 1 includes an element case 20 and a housing case 40, which supports the element case 20.

Also, the gas detector 1 has a gas detection element 60, which is a thermal-conductivity-type gas detection element, and a circuit board 41, which is electrically connected to the gas detection element 60. A microcomputer 94 is mounted on the circuit board 41.

The gas detection element 60 is accommodated in the element case 20. The circuit board 41, together with the element case 20, is accommodated in the housing case 40.

First, the structure of the housing case 40 will be described.

The housing case 40 includes a case body 42 and a case cover 44, which covers an upper end opening of the case body 42.

The case body 42 is a container which has openings at the upper and lower sides, respectively, and has a predetermined height. The case body 42 includes a circuit board holder portion 45 for holding a peripheral portion of the circuit board 41, and a holder portion 46 for holding a flange portion 38 of the element case 20.

The case body 42 also includes a flow path formation portion 43 formed at the lower center thereof and a connector 55 formed at a side portion thereof and adapted to receive electricity supplied from the outside.

The flow path formation portion 43 accommodates an inlet portion 35 of the element case 20 through which a gas-to-be-detected is introduced into and ejected from the element case 20. In this manner, the element case 20 is held by the holder portion 46 while being accommodated within the housing case 40. A seal member 47 is disposed between the case body 42 and the flange portion 38 of the element case 20 for sealing the gap therebetween.

The connector 55 is adapted to supply electricity to the circuit board 41 (and the microcomputer 94) and is mounted to the outer side surface of the case body 42. The connector 55 internally has a plurality of connector pins 56 and 57 projecting from the side wall of the case body 42. The connector pins 56 and 57 are electrically connected to the circuit board 41 (and the microcomputer 94) via respective wiring lines (not illustrated) embedded in the side wall of the case body 42.

Next, the element case 20 is described.

The element case 20 includes a connection terminal block 21, on which the gas detection element 60 is mounted, and a detection space formation member 22, which has a cylindrical wall adapted to nip a peripheral portion of the connection terminal block 21 and projecting toward a gas inlet 13 through which a gas-to-be-detected is introduced. A seal member (not shown) is disposed at a peripheral portion of the connection terminal block 21 of the element case 20 for sealing the gap between the connection terminal block 21 and the detection space formation member 22. A space enclosed by the connection terminal block 21 and the detection space formation member 22 is a detection space 39 into which a gas-to-be-detected is introduced.

The connection terminal block 21 has insertion holes through which connection terminals 24 to 28 are inserted respectively. Peripheral portions around the insertion holes are covered with an electrically insulative member.

The connection terminals 24 to 28 are electrically conductive rod-like members for electrically connecting the gas detection element 60 to circuits formed on the circuit board 41.

The detection space formation member 22 includes a sheath 36; a terminal block support portion 37, which nips a peripheral portion of the connection terminal block 21; and the flange portion 38, which is supported by the holder portion 46 of the housing case 40. The detection space formation member 22 has an inlet 34 formed at its lower end portion. The inlet 34 is an opening through which a gas-to-be-detected is introduced into the detection space 39.

The inlet portion 35 is provided in the vicinity of the inlet 34. The inlet portion 35 forms a flow path through which a gas-to-be-detected is introduced toward the gas detection element 60 and ejected. The inlet portion 35 is fitted, from a side toward the inlet 34, with a water repellent filter 29, a spacer 30, and two metallic meshes 31 and 32. These members are fixedly sandwiched between the detection space formation member 22 and a filter fixation member 33.

The water repellent filter 29 is located closest to the inlet 34. The water repellent filter 29 is a water repellent thin film for eliminating water droplets contained in gas-to-be-detected. By virtue of the water repellent filter 29, even in a very humid environment where water droplets and the like are flying, adhesion of water to the gas detection element 60 can be prevented. The water repellent filter 29 may be the type to eliminate water droplets through physical adsorption. The water repellent filter 29 can be formed by use of, for example, polytetrafluoroethylene (PTFE).

The spacer 30 is disposed on the inner circumferential wall of the filter fixation member 33 and has an opening through which gas-to-be-detected is introduced (a ring-shaped member as viewed in plane). The spacer 30 has a predetermined thickness for adjusting the relative position between the water repellent filter 29 and the two metallic meshes 31 and 32.

Each of the two metallic meshes 31 and 32 has a predetermined thickness and predetermined openings. The two metallic meshes 31 and 32 function as a flame arrester for preventing outward ejection of flame even when hydrogen gas contained in a gas-to-be-detected ignites as a result of the temperature of the heat-generating resistor of the gas detection element 60 rising above the ignition temperature of hydrogen gas.

The filter fixation member 33 has a cylindrical wall in contact with the inner wall surface of the detection space formation member 22, as well as a protrusion protruding radially inward from the inner surface of the cylindrical wall. The protrusion and the detection space formation member 22 fixedly sandwich the water repellent filter 29, the spacer 30, and the two metallic meshes 31 and 32 therebetween.

Next, the circuit board 41 is described.

The circuit board 41 is a plate-like substrate having a predetermined thickness and bears a control circuit 90 (which will be described later) for detecting a flammable gas contained in a gas-to-be-detected, and a temperature control circuit (not shown) for controlling the temperature of heat-generating elements 50 and 51.

The control circuit 90 on the circuit board 41 is electrically connected to the gas detection element 60 by means of the connection terminals 24 to 28. The temperature control circuit on the circuit board 41 is electrically connected to the heat-generating elements 50 and 51 by means of lead wires 52 and 53.

The microcomputer 94 mounted on the circuit board 41 executes a process of computing the concentration of a flammable gas contained in a gas-to-be-detected on the basis of output of the control circuit 90 provided on the circuit board 41 (sensor output computation process). Also, the microcomputer 94 executes a process of controlling the amount of heat generation (temperature) of the heat-generating elements 50 and 51 on the basis of output of the temperature control circuit (temperature control process). The microcomputer 94 consists of, at least, a memory for storing programs for executing the sensor output computation process and the temperature control process for the heat-generating elements 50 and 51, and a CPU for executing the programs stored in the memory.

Next, the heat-generating elements 50 and 51 are described.

The heat-generating elements 50 and 51 are adapted to heat the element case 20 to thereby maintain the temperature of the inner surface of the element case 20 or the temperature of the detection space 39 at a temperature higher than a predetermined temperature (at a temperature higher than at least the dew point). The heat-generating elements 50 and 51 are formed by use of, for example, a resistor used in an electronic component or the like, or a film heater. Heating by the heat-generating elements 50 and 51 prevents a gas-to-be-detected from being cooled on the inner surface of the element case 20 or in the detection space 39, thereby preventing dew condensation on the inner surface of the element case 20 or in the detection space 39 or preventing the temperature of a gas-to-be-detected from becoming unstable.

[1-2. Control Circuit]

Next, the outline of the control circuit 90 is described with reference to FIG. 2.

Figure 2:
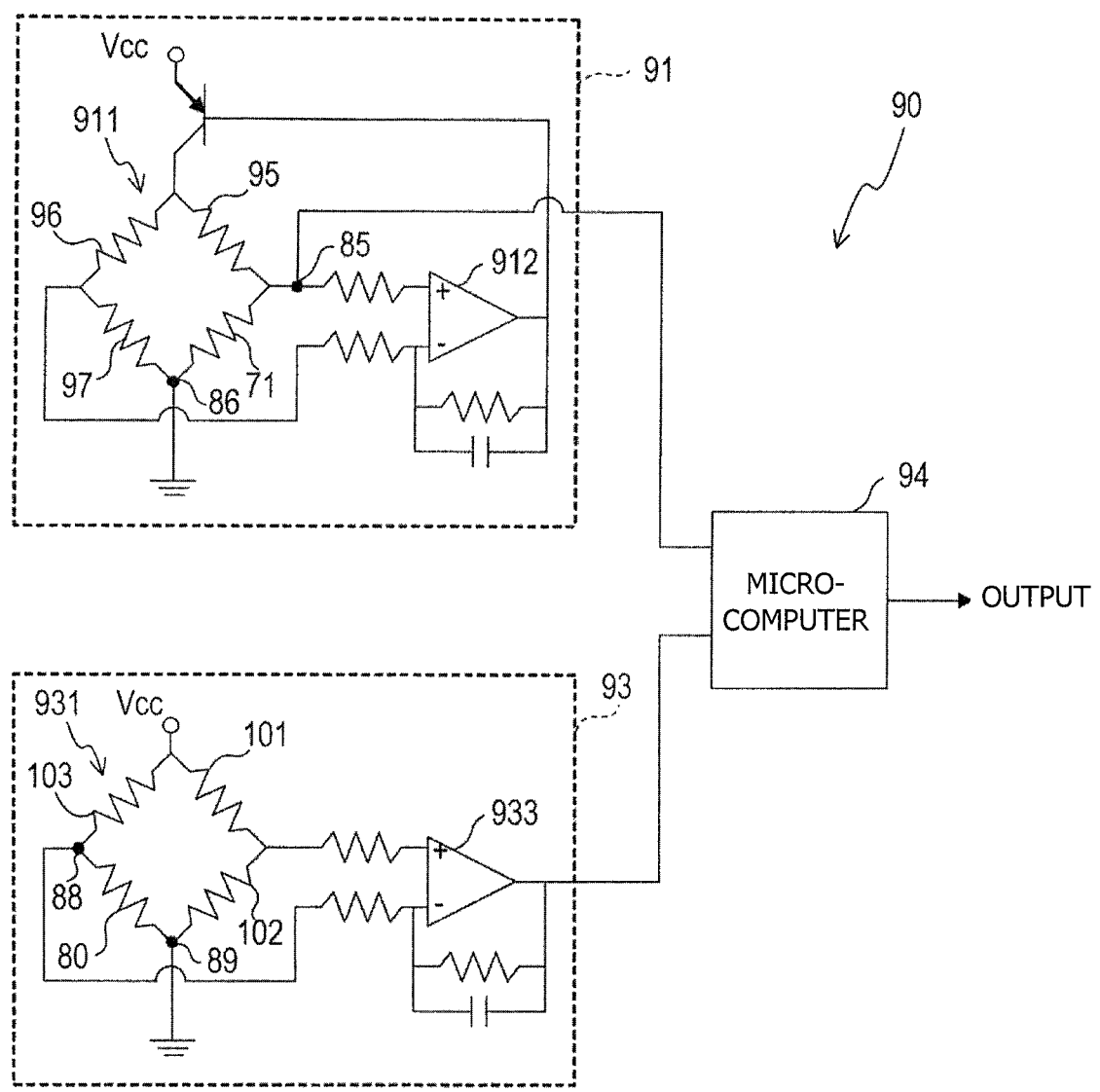
FIG. 2 is a diagram of a control circuit 90 provided on a circuit board 41.

As shown in FIG. 2, the control circuit 90 has a gas detection circuit 91 and a temperature-measuring circuit 93.

The gas detection circuit 91 has a Wheatstone bridge 911 consisting of a heat-generating resistor 71 provided in the gas detection element 60 and fixed resistors 95, 96, and 97 provided on the circuit board 41, and an operational amplifier 912 provided on the circuit board 41 and adapted to amplify a potential difference obtained from the Wheatstone bridge 911.

In the case of using the heat-generating resistor 71 whose resistance increases with its own temperature, the operational amplifier 912 operates as follows: when the temperature of the heat-generating resistor 71 increases, the operational amplifier 912 lowers its output voltage so as to maintain the heat-generating resistor 71 at a predetermined temperature; and when the temperature of the heat-generating resistor 71 lowers, the operational amplifier 912 increases its output voltage.

Since output of the operational amplifier 912 is connected to the Wheatstone bridge 911, when the temperature of the heat-generating resistor 71 rises above a predetermined temperature, the output voltage of the operational amplifier 912 lowers in order to lower the temperature of the heat-generating resistor 71, so that voltage applied to the Wheatstone bridge 911 lowers. At this time, voltage of an electrode 85, which serves as an end portion of the Wheatstone bridge 911, is detected as output of the gas detection circuit 91 by the microcomputer 94. The output value detected by the microcomputer 94 is used in the computation process for detecting a flammable gas contained in a gas-to-be-detected.

The temperature-measuring circuit 93 has a Wheatstone bridge 931 consisting of a temperature-measuring resistor 80 (which will be described later) provided in the gas detection element 60 and fixed resistors 101, 102, and 103 provided on the circuit board 41, and an operational amplifier 933 provided on the circuit board 41 and adapted to amplify a potential difference obtained from the Wheatstone bridge 931. Output of the operational amplifier 933 is detected by the microcomputer 94. The output value detected by the microcomputer 94 is used for measuring the temperature of a gas-to-be-detected and in the computation process for detecting a flammable gas contained in the gas-to-be-detected.

On the basis of the output value of the control circuit 90 having the above-mentioned configuration, the microcomputer 94 computes the concentration of a flammable gas as follows. First, the CPU (not shown) of the microcomputer 94 executes a program stored in the memory (not shown) of the microcomputer 94 by use of the output value of the gas detection circuit 91, thereby outputting a first output value substantially proportional to the concentration of a flammable gas. Since the first output value involves an output variation stemming from variation in temperature of atmosphere in the detection space 39, subsequently, the CPU outputs a second output value obtained by correcting the first output value on the basis of output from the temperature-measuring circuit 93. Further, the CPU of the microcomputer 94 outputs the concentration of a flammable gas contained in a gas-to-be-detected on the basis of the relation between the second output value and the concentration of the flammable gas which is stored in the memory (not shown) of the microcomputer 94. In this manner, the first output value is corrected on the basis of output of the temperature-measuring circuit 93; therefore, the flammable gas can be detected with accuracy. The process of computing the concentration of a flammable gas is not limited to that mentioned above, but publicly known computation means may be used as appropriate.

[1-3. Gas Detection Element]

Figure 3:
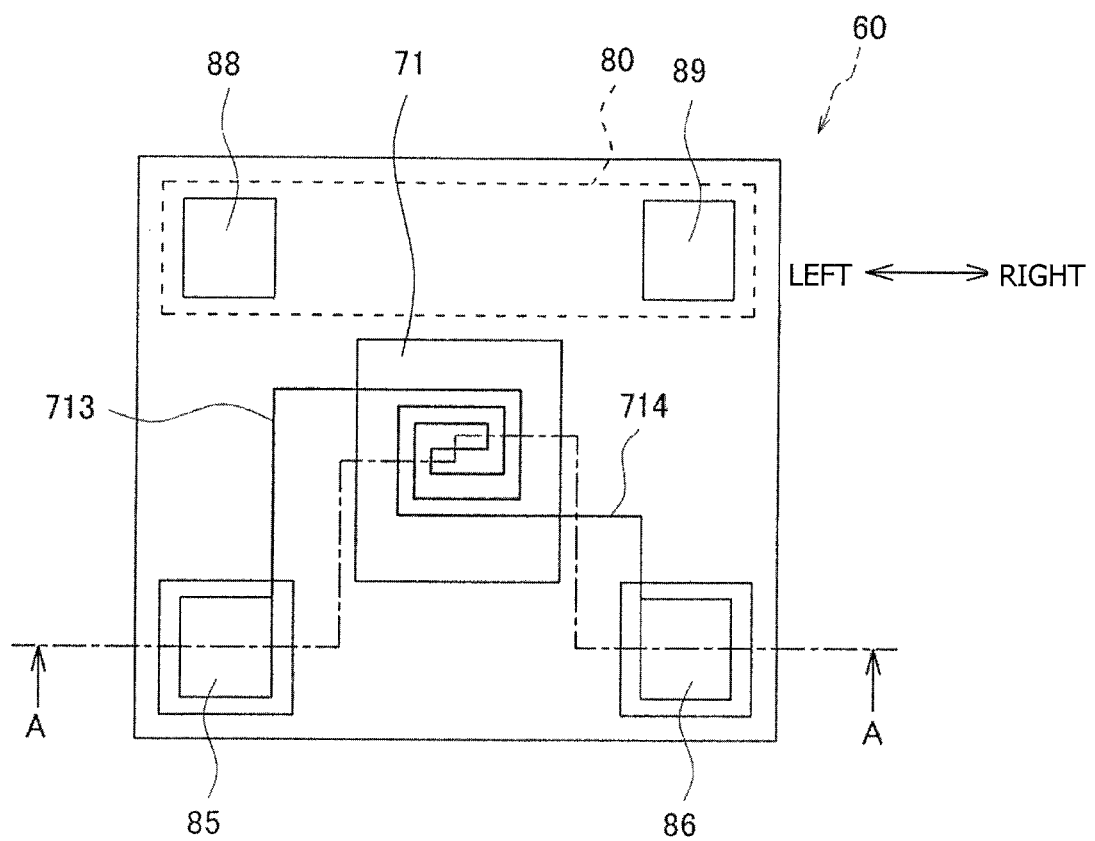
FIG. 3 is a plan view of a gas detection element 60.
Figure 4:
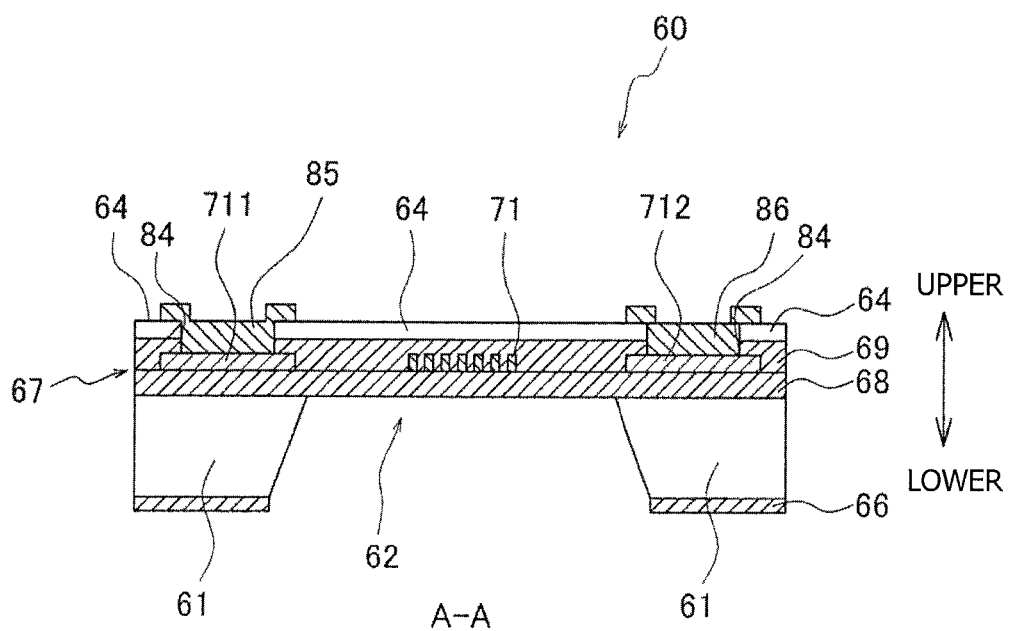
FIG. 4 is a sectional view of the gas detection element 60 taken along line A-A of FIG. 3.

Next, the composition of the gas detection element 60 is described. FIG. 3 is a plan view showing the gas detection element 60. FIG. 4 is a sectional view (taken along line A-A of FIG. 3) showing the gas detection element 60. In the plan view of FIG. 3, the horizontal direction on the paper on which FIG. 3 appears is referred to as the horizontal direction of the plan view. In the sectional view of FIG. 4, the vertical direction on the paper on which FIG. 4 appears is referred to as the vertical direction of the sectional view.

The gas detection element 60 is manufactured by use of the micromachining technique. As shown in FIG. 4, the gas detection element 60 has a semiconductor substrate 61 of silicon, and insulation layers (an upper insulation layer 67 and a lower insulation layer 66) provided on the upper and lower sides, respectively, of the semiconductor substrate 61. The upper insulation layer 67 is formed on the front side of the semiconductor substrate 61 of silicon, and the lower insulation layer 66 is formed on the back side of the semiconductor substrate 61. Also, a protection layer 64 is formed on the surface of the upper insulation layer 67. The upper insulation layer 67 consists of an insulation layer 68 formed on the front side of the semiconductor substrate 61 of silicon, and an insulation protection layer 69 formed on the surface of the insulation layer 68. The gas detection element 60 also has the heat-generating resistor 71.

The semiconductor substrate 61 of silicon has a cavity 62 formed in a region located under the heat-generating resistor 71. The cavity 62 is formed by removing a portion of the semiconductor substrate 61 of silicon in such a manner as to form an opening. A portion of the upper insulation layer 67 is exposed to the cavity 62 from above. The heat-generating resistor 71 is embedded in the upper insulation layer 67 in a region corresponding to the cavity 62.

By virtue of the above configuration, the heat-generating resistor 71 is heat-insulated from the surrounding by means of the cavity 62. Thus, the heat-generating resistor 71 raises and lowers temperature in a short period of time. Therefore, the thermal capacity of the gas detection element 60 can be reduced.

Wiring films 711 and 712 are formed on the same plane as that on which the heat-generating resistor 71 is formed. The wiring films 711 and 712 and wiring lines 713 and 714 (for the wiring lines 713 and 714, see FIG. 3) are embedded in the upper insulation layer 67. The upper insulation layer 67 is formed from an electrically insulative material, for example, silicon oxide ($SiO_2$) or silicon nitride ($Si_3N_4$). The upper insulation layer 67 may be formed such that a plurality of layers are formed from the same material or such that a plurality of layers are formed from different materials. In the present embodiment, at least the insulation protection layer 69 is formed from silicon nitride ($Si_3N_4$).

The protection layer 64 having a predetermined thickness is formed on the upper surface of the upper insulation layer 67. The protection layer 64 is formed of, for example, an oxide film containing at least one of Ta, Nb, and Hf (an oxide film mainly containing tantalum oxide ($Ta_2O_5$) in the present embodiment). The protection layer 64 is provided in such a manner as to cover the heat-generating resistor 71, the wiring films 711 and 712, and the wiring lines 713 and 714 for preventing contamination and damage thereof.

The heat-generating resistor 71 is formed spirally (see FIG. 3) and varies in temperature and resistance according to the temperature of a gas-to-be-detected (more specifically, thermal conduction to a flammable gas). The heat-generating resistor 71 is formed from an electrically conductive material having a high temperature coefficient of resistance, for example, platinum (Pt). In the case of detecting hydrogen gas, which is a flammable gas, the amount of heat removed by the heat-generating resistor 71 through thermal conduction to hydrogen gas corresponds to the concentration of hydrogen gas. Therefore, the concentration of hydrogen gas can be detected on the basis of a change in electrical resistance of the heat-generating resistor 71.

Notably, the temperature of a gas-to-be-detected has an effect on a change in resistance of the heat-generating resistor 71. Thus, by use of the temperature detected on the basis of electric resistance of the temperature-measuring resistor 80 (FIG. 3), which will be described later, the concentration of a gas-to-be-detected which is detected on the basis of a change in electric resistance of the heat-generating resistor 71 is corrected, whereby accuracy in detecting the concentration of the gas-to-be-detected can be improved.

Next, the left end of the heat-generating resistor 71 is electrically connected to the electrode 85 (FIG. 3) via the wiring line 713 (FIG. 3) and the wiring film 711 (FIG. 4), which are embedded in the upper insulation layer 67 (FIG. 4) and are integrally formed with the heat-generating resistor 71. The right end of the heat-generating resistor 71 is electrically connected to a ground electrode 86 (FIG. 3) via the wiring line 714 (FIG. 3) and the wiring film 712 (FIG. 4), which are embedded in the upper insulation layer 67 and are integrally formed with the heat-generating resistor 71. The electrode 85 and the ground electrode 86 are terminals for external connection of the wiring lines connected to the heat-generating resistor 71 and are exposed through respective contact holes 84 (FIG. 4). The electrode 85 and the ground electrode 86 are formed from, for example, aluminum (Al) or gold (Au).

The temperature-measuring resistor 80 (FIG. 3) is adapted to detect the temperature of a gas-to-be-detected existing in the detection space 39 (see FIG. 1). The temperature-measuring resistor 80 is formed between the upper insulation layer 67 (FIG. 4) and the protection layer 64 (FIG. 4) and on a plane in parallel with the semiconductor substrate 61 of silicon. The temperature-measuring resistor 80 is formed from a metal whose electric resistance varies in proportion to temperature, for example, platinum (Pt).

The temperature-measuring resistor 80 is electrically connected to an electrode 88 (FIG. 3) and a ground electrode 89 (FIG. 3). The electrode 88 and the ground electrode 89 are exposed through respective contact holes (not shown). The electrode 88 and the ground electrode 89 are formed form, for example, aluminum (Al) or gold (Au).

[1-4. Manufacturing Process for Gas Detection Element]

Figure 5:
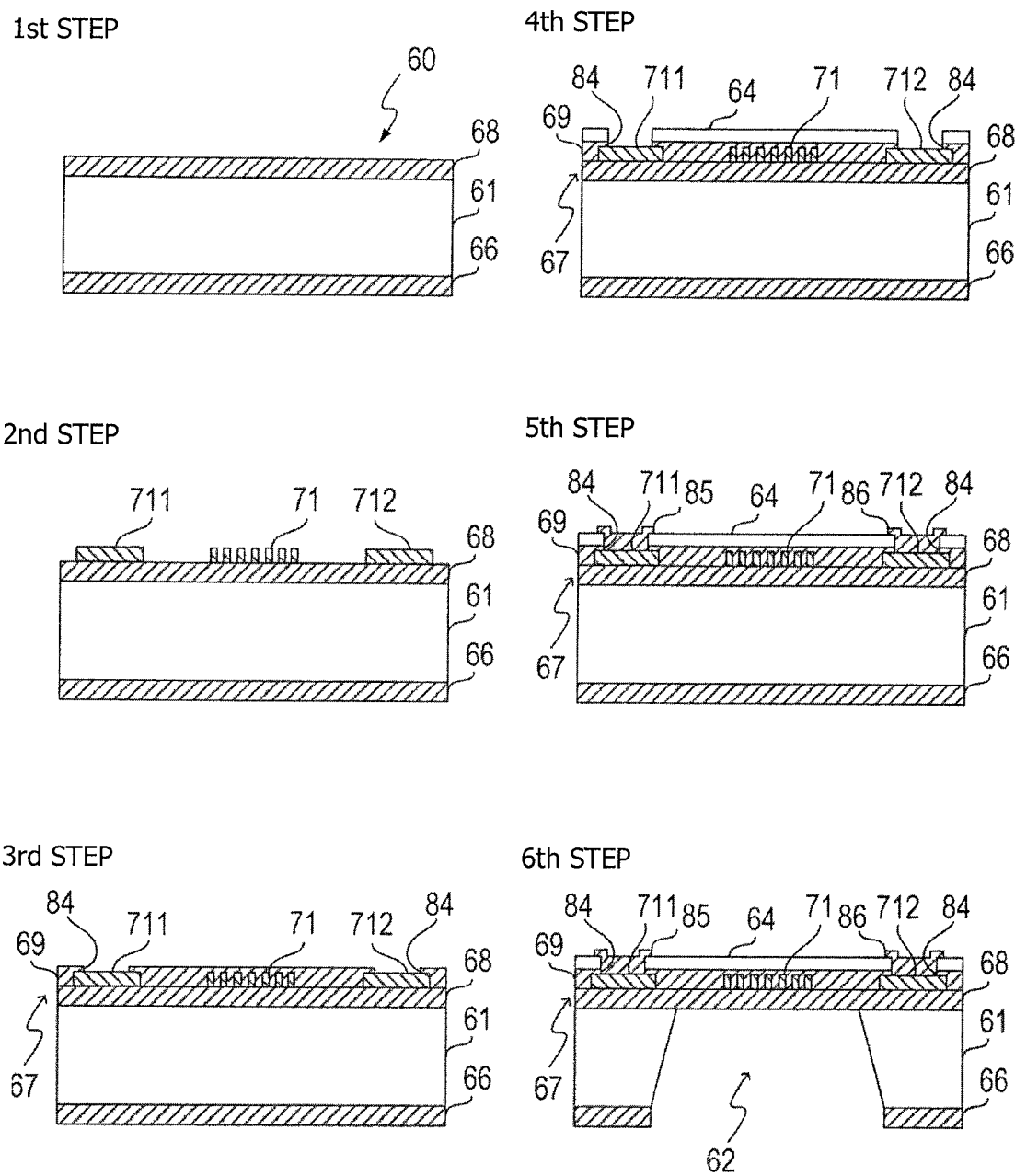
FIG. 5 is a view showing steps of producing the gas detection element 60.

Next, a process of manufacturing the gas detection element 60 is described with reference to FIG. 5.

[1-4-1. Step of Forming Insulation Layer 68 and Lower Insulation Layer 66 (First Step)]

The semiconductor substrate 61 of silicon is prepared. The semiconductor substrate 61 of silicon is cleaned and then subjected to a thermal oxidation process. By this process, a silicon oxide film ($SiO_2$ film) having a thickness of 100 [nm] is formed on each of the front and back surfaces of the semiconductor substrate 61 of silicon. Then, a silicon nitride film ($Si_3N_4$ film) having a thickness of 200 [nm] is formed, by a low-pressure CVD process, on each of the silicon oxide films formed on the upper and lower sides of the semiconductor substrate 61 of silicon.

By this procedure, the silicon oxide film and the silicon nitride film formed on the upper side of the semiconductor substrate 61 of silicon collectively serve as the insulation layer 68, and the silicon oxide film and the silicon nitride film formed on the lower side of the semiconductor substrate 61 of silicon collectively serve as the lower insulation layer 66.

[1-4-2. Step of Forming Heat-Generating Resistor 71 and Wiring Films 711 and 712 (Second Step)]

After the insulation layer 68 and the lower insulation layer 66 are formed as mentioned above, in an atmosphere having a temperature of 300[° C.], a tantalum film (Ta film) having a thickness of 20 [nm] is formed on the surface of the insulation layer 68 by a sputtering method; next, a platinum film (Pt film) having a thickness of 400 [nm] is formed on the tantalum film in an overlaying manner by a sputtering method; and then, a tantalum film having a thickness of 20 [nm] is again formed on the platinum film in an overlaying manner by a sputtering method. The tantalum films are adapted to enhance adhesion strength between the platinum film and the insulation layer 68.

Subsequently, by a photolithographic process, portions of the tantalum films and the platinum film which do not correspond to the heat-generating resistor 71 and the wiring films 711 and 712 are etched away. By this process, the heat-generating resistor 71 and the wiring films 711 and 712 are formed on the surface of the insulation layer 68. The wiring films 711 and 712 and the heat-generating resistor 71 have a temperature coefficient of resistance of about 2,000 [ppm/° C.]. In this step, the temperature-measuring resistor 80 is also formed on the surface of the insulation layer 68 by a method similar to that used to form the heat-generating resistor 71.

[1-4-3. Step of Forming Insulation Protection Layer 69 (Third Step)]

After the heat-generating resistor 71 and the wiring films 711 and 712 are formed as mentioned above, a silicon oxide layer ($SiO_2$ layer) having a thickness of 100 [nm] is formed on the surface of the insulation layer 68 by a plasma CVD process in such a manner as to cover the heat-generating resistor 71 and the wiring films 711 and 712. Further, on the silicon oxide layer, a silicon nitride layer ($Si_3N_4$ layer) having a thickness of 200 [nm] is formed in an overlaying manner by a low-pressure CVD process. The processes for forming these layers are carried out at a temperature lower than that for the processes for forming the insulation layer 68, the lower insulation layer 66, and the wiring films 711 and 712.

Next, portions of the silicon nitride layer and the silicon oxide layer which correspond to the wiring films 711 and 712 are etched away by a photolithographic process. By this process, the insulation protection layer 69 having the contact holes 84 is formed on the surface of the insulation layer 68 in such a manner as to cover the heat-generating resistor 71. Also, by a similar etching process, contact holes (not shown) for the temperature-measuring resistor 80 are formed.

[1-4-4. Step of Forming Protection Layer 64 (Fourth Step)]

After formation of the insulation protection layer 69 as mentioned above, an oxide film mainly containing tantalum oxide ($Ta_2O_5$) and having a thickness of 15 [nm] is formed in an overlaying manner by a sputtering method. This oxide film serves as the protection layer 64.

Then, portions of the oxide film mainly containing tantalum oxide ($Ta_2O_5$) which correspond to the wiring films 711 and 712 are etched away by a photolithographic process.

[1-4-5. Step of Forming Electrodes 85 and 86 (Fifth Step)]

After the protection layer 64 is formed as mentioned above, a chromium film (Cr film) having a thickness of 20 [nm] is formed in an overlaying manner on the protection layer 64 by a sputtering method. Then, a gold film (Au film) having a thickness of 600 [nm] is formed on the chromium film in an overlaying manner by a sputtering method.

Subsequently, portions of an electrode layer consisting of the gold film and the chromium film which do not correspond to the contact holes 84 are etched away by a photolithographic process. By this procedure, the electrodes 85 and 86 are formed in and around the respective contact holes 84. In this step, the electrode 88 and the ground electrode 89 are also formed in and around the respective non-illustrated contact holes.

[1-4-6. Step of Forming Cavity 62 (Sixth Step)]

After the electrodes 85 and 86 are formed as mentioned above, a portion of the lower insulation layer 66 which corresponds to the heat-generating resistor 71 is etched away. Then, a portion of the semiconductor substrate 61 of silicon which corresponds to the etched-away portion is etched away by use of tetramethylammonium hydroxide, thereby exposing a portion of the insulation layer 68 which corresponds to the heat-generating resistor 71. By this procedure, the cavity 62 is formed in portions of the semiconductor substrate 61 of silicon and the lower insulation layer 66 which correspond to the heat-generating resistor 71.

[1-4-7. "Thickness" of Protection Layer 64]

Meanwhile, the "thickness" of the protection layer 64 is described with reference to FIG. 6.

Figure 6:
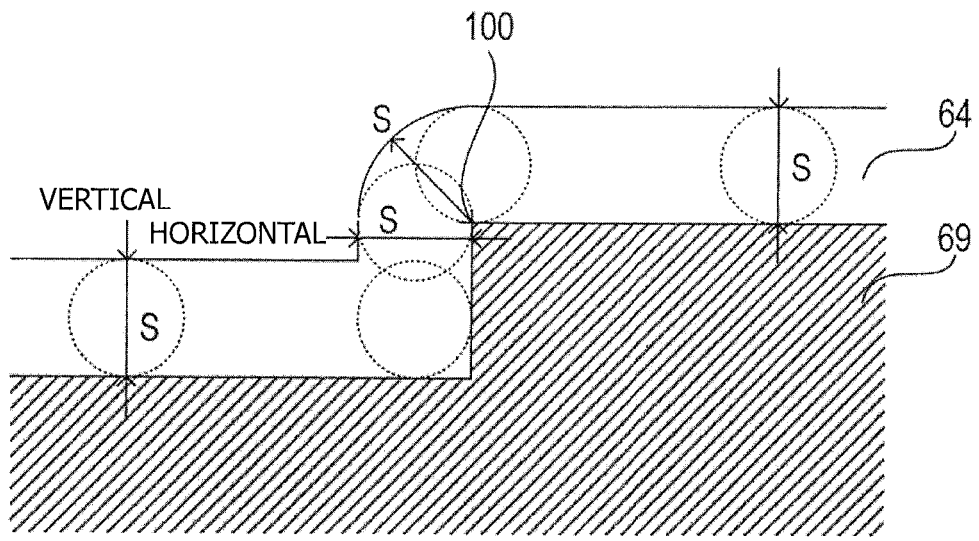
FIG. 6 is a view for describing a definition of the thickness of a protection layer 64.

As a premise, the surface of the insulation protection layer 69 is rugged (uneven) as shown in FIG. 6, since the heat-generating resistor 71, for example, exists under the surface.

For example, that the protection layer 64 has a thickness of S [nm] means that the trajectory of a circle having a diameter of S resulting from the circle rolling on the surface of the insulation protection layer 69 is contained on the inside of the surface of the protection layer 64. That is, as shown in FIG. 6, both the thickness along the vertical direction and the thickness along the horizontal direction are S [nm]. Further, the thickness from an edge 100 of the insulation protection layer 69 (the distance from the edge 100 to the surface of the protection layer 64) is also S [nm].

Figure 7:
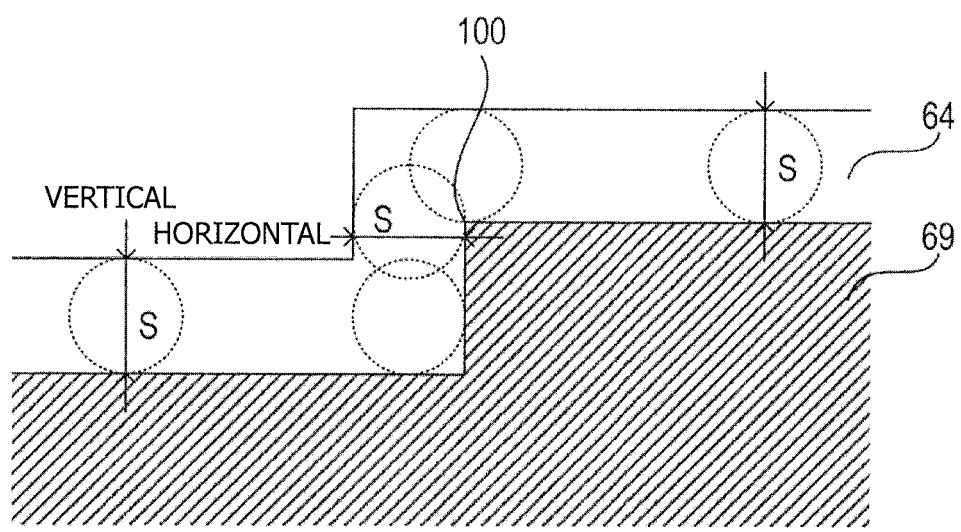
FIG. 7 is a view for describing another definition of the thickness of the protection layer 64.

As shown in FIG. 7, the rugged surface of the protection layer 64 may have an edge corresponding to an edge of the rugged surface of the insulation protection layer 69.

In the present embodiment, since the surface of the gas detection element 60 is covered with the protection layer 64 formed of an oxide film mainly containing tantalum oxide ($Ta_2O_5$), the gas detection element 60 has excellent alkali resistance and condensed-water resistance. That is, since the protection layer 64 has excellent condensed-water resistance, even when water droplets adhere thereto, the morphology thereof does not change from dense to porous. Thus, since a change in property of the protection layer 64, which would otherwise be caused by adhesion of water droplets, can be reduced in the gas detection element 60, even when water droplets adhere to the outermost surface layer of the gas detection element 60, impurities can be prevented from entering the protection layer 64 (the outermost surface layer), whereby a change in thermal capacity of the gas detection element 60 can be reduced.

Further, since the protection layer 64 is formed by a sputtering method, the protection layer 64 is very dense (impermeable to gas, for example). Therefore, as compared with, for example, the case where the protection layer 64 has a porous structure, there can be restrained the entry, into the protection layer 64, of impurities (e.g., organic silicon) contained in an environmental atmosphere which contains a gas-to-be-detected.

[1-5. Evaluation Test]

Next will be described the results of tests for evaluating the alkali resistance and condensed-water resistance of a gas detector to which the present invention is applied.

[1-5-1. Test for Evaluation of Alkali Resistance]

This test was carried out for evaluation of the alkali resistances of one gas detection element of the present invention (Example) and four gas detection elements for comparison (Comparative Examples).

The gas detection element of Example 1 was produced so as to include a protection layer formed of an oxide film mainly containing tantalum oxide. The gas detection element of Comparative Example 1 was produced so as to include no protection layer. The gas detection element of Comparative Example 2 was produced so as to include a protection layer mainly containing alumina ($Al_2O_3$). The gas detection element of Comparative Example 3 was produced so as to include a protection layer mainly containing silicon oxide ($SiO_2$). The gas detection element of Comparative Example 4 was produced so as to include a protection layer mainly containing silicon carbide (SiC).

This test was carried out on six samples for each of the gas detection elements.

The alkali resistance evaluation test was performed through the following procedure.

Firstly, an aqueous sodium chloride solution ($10^{-5}$ [mol/L]) was added dropwise (1 [μL]) onto the upper surface of the heat-generating resistor of each gas detection element, and the solution was dried by heating of the heat-generating resistor through energization for one minute. This operation was carried out twice. The temperature of the energized heat-generating resistor is adjusted to 400[° C.].

Thereafter, each gas detection element was placed in an environment of 85 [° C.] and 85 [% RH], and the heat-generating resistor was energized for 400 hours so that the temperature thereof was maintained at 400[° C.].

After the elapse of 400 hours, each gas detection element was observed for determining whether or not breakage occurred in a thin film portion. When no breakage occurred in all the six samples, rating "OK" was assigned, whereas when breakage occurred in at least one of the six samples, rating "NG" was assigned.

Table 1 shows the test results of the gas detection elements.

TABLE 1

| Sample No. | Protection layer | Number of broken samples | Evaluation |
|---|---|---|---|
| Example 1 | Mainly containing tantalum oxide ($Ta_2O_5$) | 0/6 | OK |
| Comparative Example 1 | No protection layer | 6/6 | NG |
| Comparative Example 2 | Mainly containing alumina ($Al_2O_3$) | 0/6 | OK |
| Comparative Example 3 | Mainly containing silicon oxide ($SiO_2$) | 3/6 | NG |
| Comparative Example 4 | Mainly containing silicon carbide (SiC) | 3/6 | NG |

As shown in the test results, the gas detection elements of Example 1 and Comparative Example 2 were evaluated as "OK" (i.e., no breakage in all the six samples), whereas the gas detection elements of Comparative Examples 1, 3, and 4 were evaluated as "NG" (breakage in at least one sample).

These test results indicate that the gas detection element of Example 1 (according to the present invention) exhibits excellent alkali resistance.

[1-5-2. Test for Evaluation of Condensed-Water Resistance]

Subsequently, a test was carried out for evaluation of the condensed-water resistances of the gas detection elements of Example 1 and Comparative Example 2, which had been evaluated as "OK" in the aforementioned alkali resistance evaluation test.

Specifically, gas detectors were prepared from the gas detection element of Example 1 and the gas detection element of Comparative Example 2, and a variation in sensor output was determined for each of the gas detectors on the basis of the sensor outputs measured before and after placement of the gas detector in an environment where dew condensation occurs.

This test was carried out on three samples for each of the gas detectors of Example 1 and Comparative Example 2.

Figure 8:
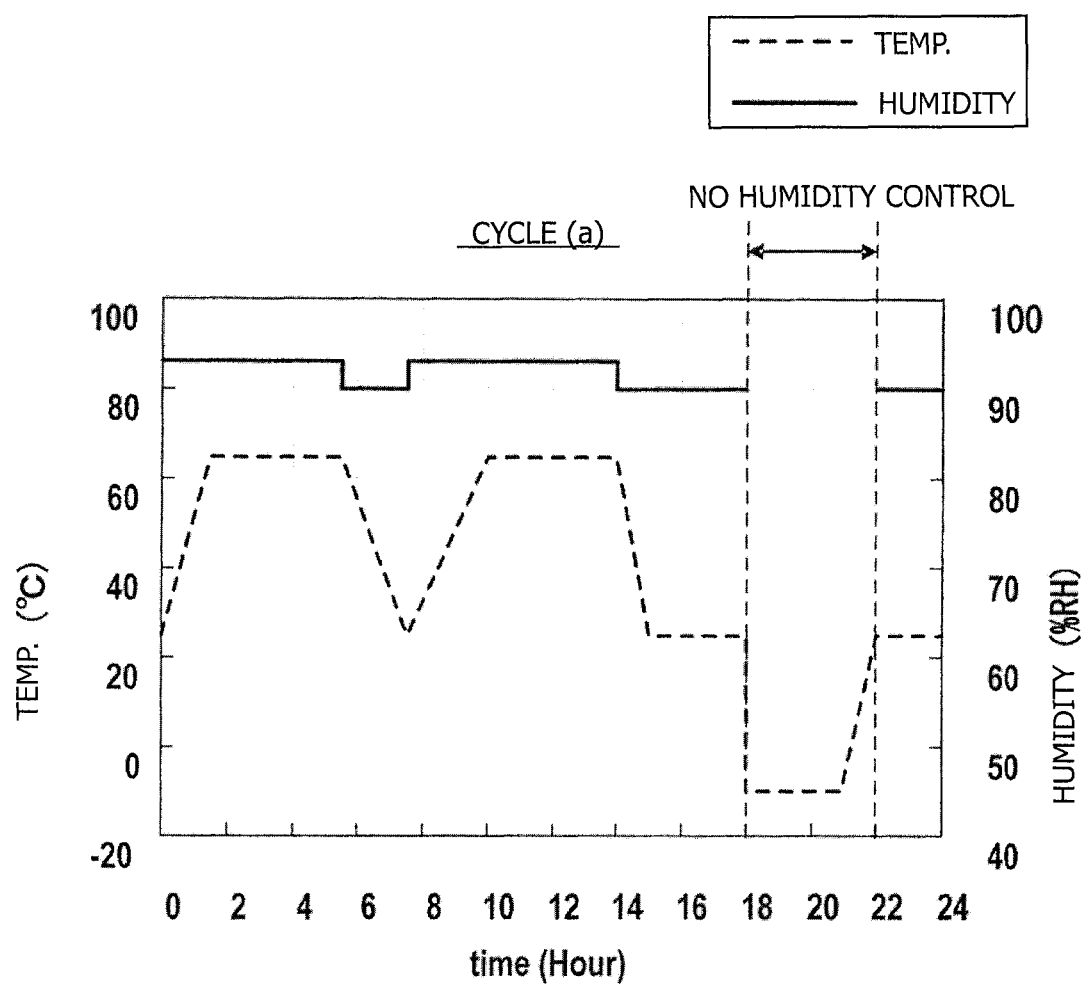
FIG. 8 is a schematic view for describing the temperature and humidity of cycle (a) in a test for evaluation of condensed-water resistance.
Figure 9:
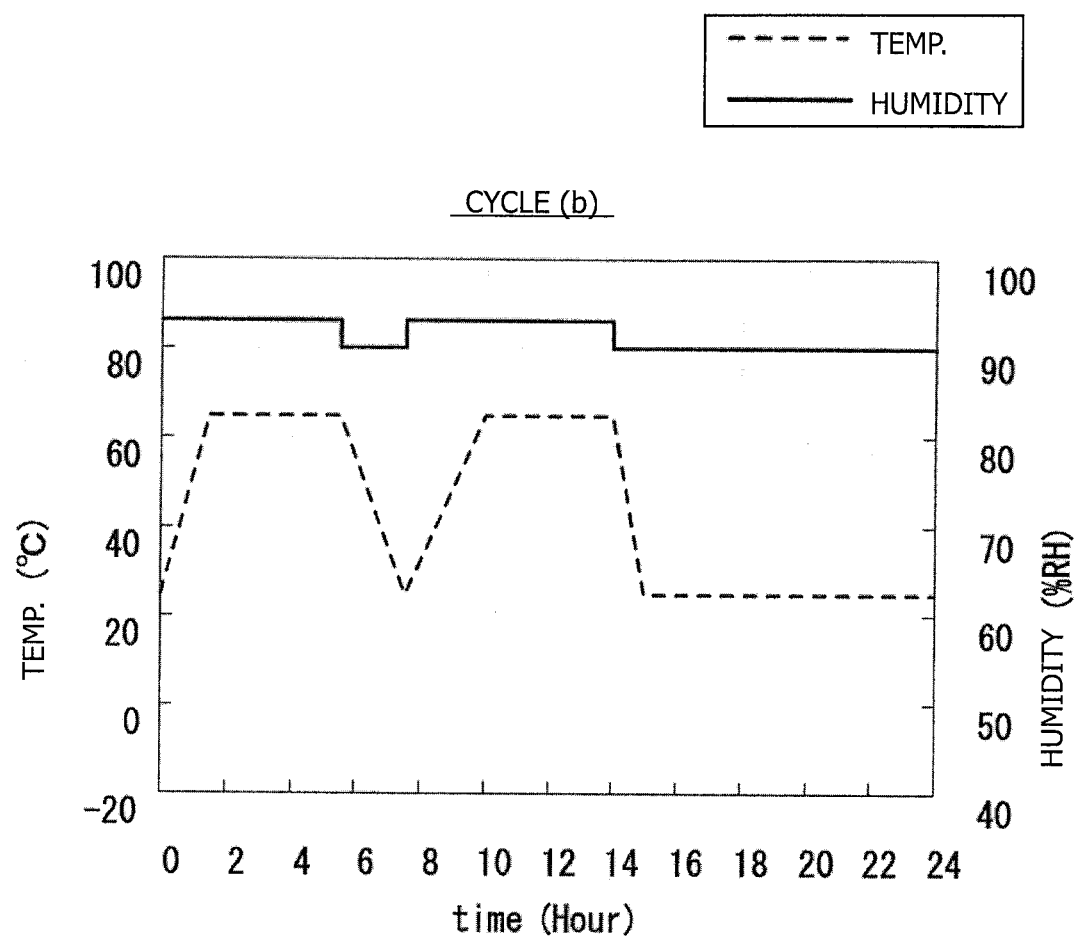
FIG. 9 is a schematic view for describing the temperature and humidity of cycle (b) in the test for evaluation of condensed-water resistance.

The condensed-water resistance evaluation test corresponds to the temperature-humidity combination cycle test according to "JASO D 014-4:2006." Specifically, each gas detector was placed alternately in different temperature-humidity environments (i.e., cycle (a) shown in FIG. 8 and cycle (b) shown in FIG. 9), and a variation in sensor output was determined for the gas detector on the basis of the sensor outputs measured before and after placement of the gas detector in these environments. The present applicant performed the condensed-water resistance evaluation test while confirming that dew condensation necessarily occurred on the surface of the detection element.

In this test, each gas detector was subjected to cycles (a) and (b) alternately (five times for each cycle), and the gas detector was energized at a point in time when a high temperature (65° C.) was maintained in the fifth cycle (b).

Before and after placement of the gas detector in the aforementioned environments, the sensor outputs were measured under the following conditions: gas composition: $H_2O$=50% RH, Air=bal., gas temperature: 25[° C.], gas flow rate: 5 [L/min], pressure: atmospheric pressure.

For evaluation of the gas detector in this test, a variation in sensor output was determined on the basis of the sensor outputs measured before and after placement of the gas detector in the environments where dew condensation occurs. When a variation in sensor output falls within a range of ±0.2 [$H_2$%], rating "OK" was assigned, whereas when a variation in sensor output falls outside a range of ±0.2 [$H_2$%], rating "NG" was assigned.

Table 2 shows the test results of the gas detection elements.

TABLE 2

| Sample No. | Protection layer | Variation in output [$H_2$ %] | | | Evaluation |
|---|---|---|---|---|---|
| | | First | Second | Third | |
| Example 1 | Mainly containing tantalum oxide ($Ta_2O_5$) | −0.04 | −0.03 | −0.07 | OK |
| Comparative Example 2 | Mainly containing alumina ($Al_2O_3$) | −0.24 | −0.21 | −0.28 | NG |

As shown in the test results, the gas detection element of Example 1 was evaluated as "OK" (a variation within a range of ±0.2 [$H_2$%] in all the three samples), whereas the gas detection element of Comparative Example 2 was evaluated as "NG" (a variation outside a range of ±0.2 [$H_2$%] in all the three samples).

Figure 10:
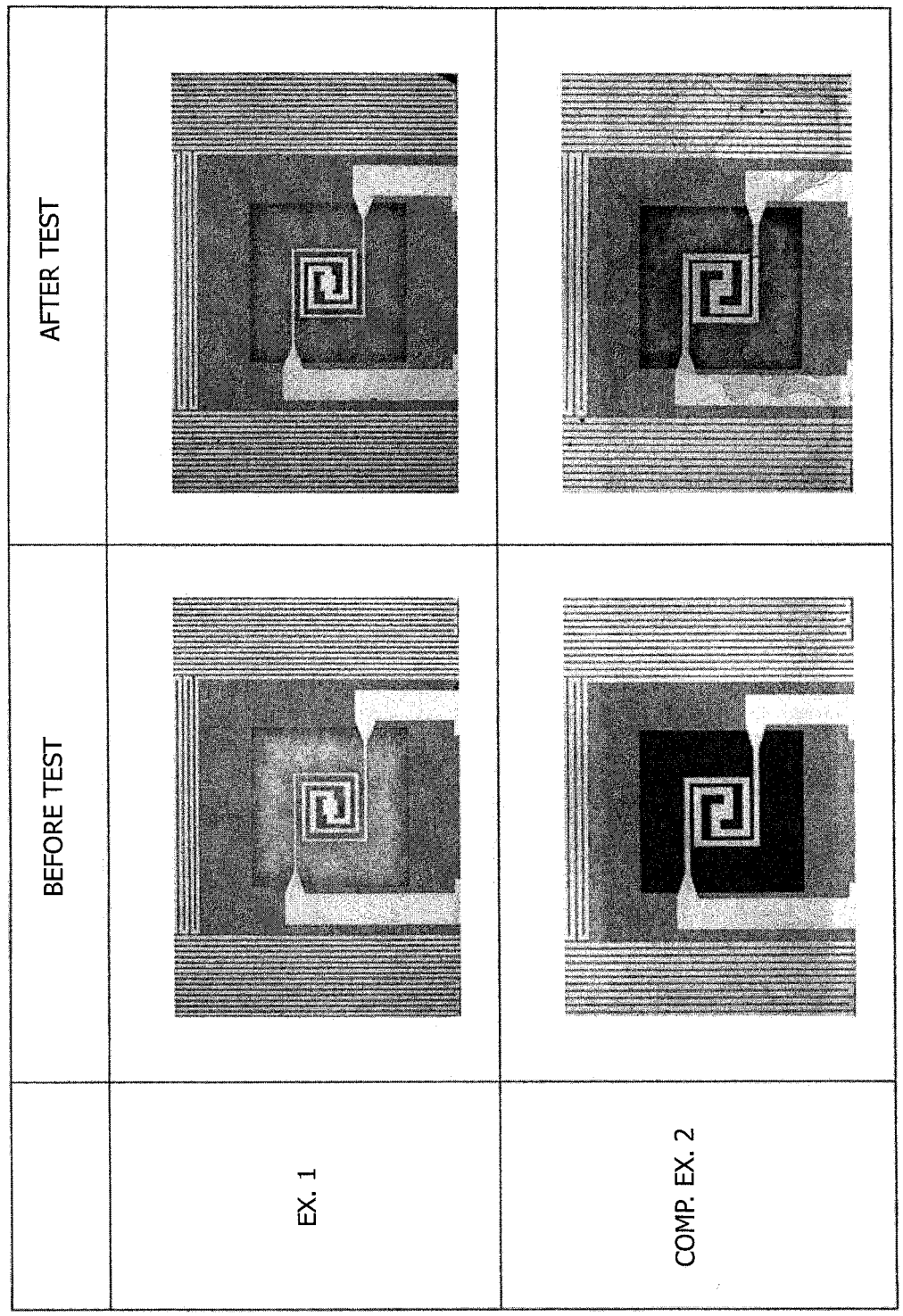
FIG. 10 is a photographic images of the appearances of gas detection elements before and after the test for evaluation of condensed-water resistance.

FIG. 10 shows photographic images of the appearances of the gas detection elements of Example 1 and Comparative Example 2 before and after the test.

As illustrated in FIG. 10, the gas detection element of Example 1 showed no considerable difference in appearance between before and after the test; i.e., the protection layer was not eroded by water droplets resulting from dew condensation.

In contrast, the gas detection element of Comparative Example 2 showed a patchy (dotted) appearance after the test; i.e., a difference in appearance between before and after the test. This is because, the protection layer was eroded by water droplets resulting from dew condensation, and the morphology of the protection layer changed from dense to porous. When such a change in property occurs in the protection layer, entry of impurities into pores of the porous protection layer causes a change in thermal capacity of the gas detection element, leading to an error in the output of the gas detection element. Thus, the gas detection element of Comparative Example 2 showed a variation in sensor output (on the basis of the sensor outputs before and after the test) falling outside a specific range, and was evaluated as "NG" (see Table 2).

These test results indicate that the gas detection element of Example 1 (according to the present invention) exhibits condensed-water resistance superior to that of the gas detection element of Comparative Example 2.

Similar effects were obtained in a gas detection element including a protection layer mainly containing niobium oxide ($Nb_2O_5$) or hafnium oxide ($HfO_2$).

[1-6. Effects]

As described above, the gas detection element 60, which is provided in the gas detector 1 of the present embodiment, has the protection layer 64 formed of an oxide film mainly containing tantalum oxide ($Ta_2O_5$).

Even when water droplets adhere to the surface of the gas detection element 60, erosion of the protection layer 64 by the water droplets can be prevented. That is, since the protection layer 64 has excellent condensed-water resistance, even when water droplets adhere thereto, the morphology thereof does not change from dense to porous. Thus, since a change in property of the protection layer 64, which would otherwise be caused by adhesion of water droplets, can be reduced in the gas detector 1, even when water droplets adhere to the outermost surface layer of the gas detection element 60, impurities can be prevented from entering the protection layer 64 (the outermost surface layer), whereby a change in thermal capacity of the gas detection element 60 can be reduced.

The protection layer 64, which is formed of an oxide material, exhibits excellent alkali resistance. Therefore, for example, even when an alkaline substance adheres to the surface of the gas detection element 60, erosion by the alkaline substance can be prevented.

Furthermore, the protection layer 64, which has gas impermeability (a dense structure), can prevent entry thereinto of impurities (e.g., an organic silicon compound) contained in an environmental atmosphere containing a gas-to-be-detected. For example, when the protection layer 64 has a porous structure (i.e., gas permeability), impurities are likely to adhere to the protection layer 64 through entry into pores. However, the gas detection element 60 of the present embodiment is free from such adhesion; i.e., the configuration of the embodiment can prevent impurities from entering the protection layer 64 (the outermost surface layer) of the gas detection element 60, to thereby reduce a change in thermal capacity.

As described above, the gas detection element 60 of the gas detector 1 of the present embodiment has excellent alkali resistance and condensed-water resistance. Thus, according to the gas detector 1 of the present embodiment, the output of the gas detection element 60 is stabilized and becomes accurate, whereby high gas detection accuracy can be achieved.

In the gas detection element 60, the insulation protection layer 69 of the upper insulation layer 67 is formed of silicon nitride ($Si_3N_4$). Since silicon nitride has excellent corrosion resistance and stability, the durability of the gas detection element 60 can be enhanced in combination with excellent alkali resistance and condensed-water resistance being attained through provision of the protection layer 64.

The protection layer 64 has a thickness of 15 [nm], which is greater than one-fiftieth of the thickness (400 [nm]) of the heat-generating resistor 71. When the thickness of the protection layer 64 is determined to be such a level, generation of holes (spots or pores) can be prevented in the protection layer 64.

The protection layer 64 is formed so as to have a thickness of 5 to 200 nm (15 [nm] in the present embodiment). When the lower limit of the thickness of the protection layer 64 is determined as described above, generation of holes (spots or pores) can be prevented in the protection layer 64. Meanwhile, when the upper limit of the thickness of the protection layer 64 is determined as described above, an excessive increase in thickness of the protection layer 64 can be prevented, to thereby avoid a problem of poor flexibility of the protection layer 64 against, for example, thermal expansion and contraction.

The thickness of the protection layer 64 is the distance between the surface of the upper insulation layer 67 and the surface of the protection layer 64 which comes into contact with a gaseous atmosphere. That is, the surface of the upper insulation layer 67 has irregularities to a certain extent stemming from the existence of the heat-generating resistor 71 within the upper insulation layer 67, and the protection layer 64 is formed in such a manner as to have a specific thickness as measured along the irregular surface profile.

Thus, the distance from an edge of the irregular surface profile of the upper insulation layer 67 to the surface of the protection layer 64 reliably falls within the required range, thereby preventing variation in the effect of provision of the protection layer 64, which could otherwise result from the irregularities.

In the gas detection element 60 of the present embodiment, the protection layer 64 is formed through a sputtering process. Thus, the protection layer 64, which is formed as a dense film, can prevent entry thereinto of impurities (e.g., an organic silicon compound) contained in an environmental atmosphere containing a gas-to-be-detected. This configuration can prevent impurities from entering the protection layer 64 (the outermost surface layer) of the gas detection element 60, to thereby reduce a change in thermal capacity.

The gas detection element 60 is a thermal-conductivity-type gas detection element. The thermal-conductivity-type gas detection element, which is provided with the protection layer 64, exhibits excellent alkali resistance and condensed-water resistance. In particular, the thermal-conductivity-type gas detection element is conceived to take greater advantage of the effect of provision of the protection layer 64.

In order to detect a gas-to-be-detected having a low concentration on the order of ppm (parts per million), the output of the thermal-conductivity-type gas detection element must be amplified. Therefore, a smaller error in the output is more preferred.

Thus, the gas detection element 60 of the present embodiment is advantageous in that, since a change in property of the protection layer 64, which would otherwise be caused by water droplets, can be prevented, a change in thermal capacity, which may be due to entry of impurities, can also be reduced, resulting in a reduction in error.

[1-7. Correspondence to Claims]

Now will be described the correspondence between terms used in claims and the present embodiment.

The upper insulation layer 67 corresponds to an example of the insulation layer; the circuit board 41 corresponds to an example of the control means; and the protection layer 64 corresponds to an example of the oxide film.

2. Other Embodiments

While the present invention has been described with reference to the above embodiment, the present invention is not limited thereto, but may be embodied in various other forms without departing from the scope of the invention.

Figure 11:
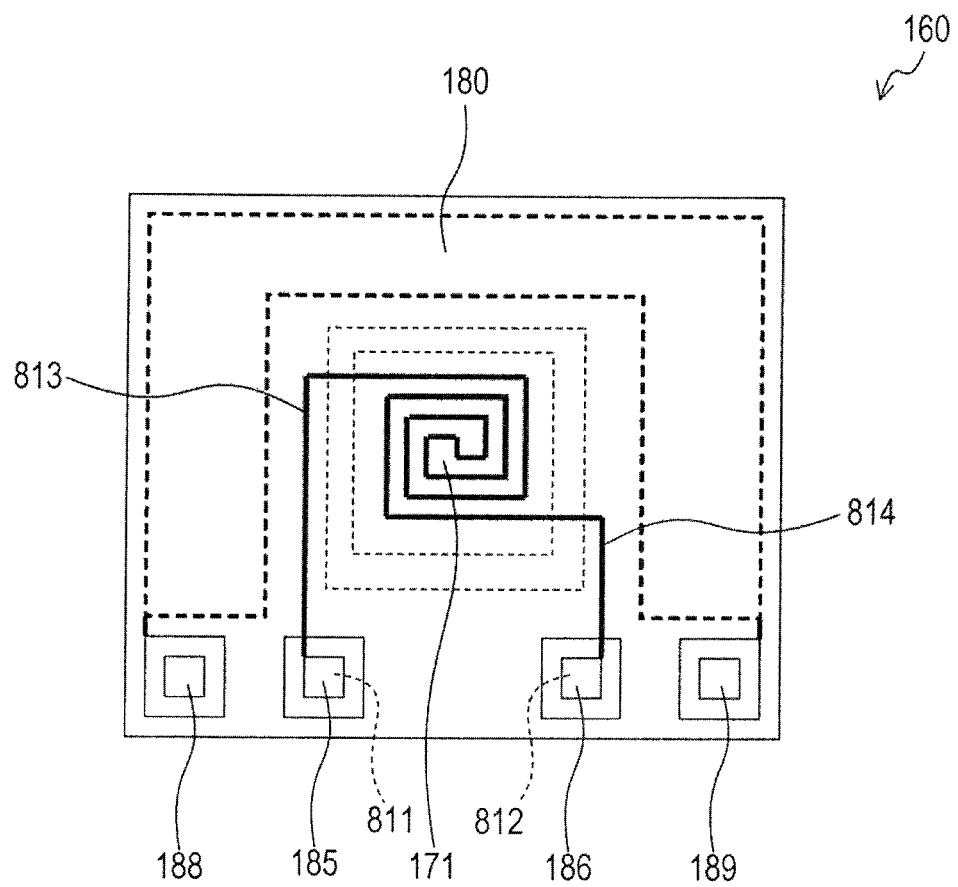
FIG. 11 is a plan view of a second gas detection element 160.

For example, in the above-described embodiment, the gas detection element 60 has a configuration such that the temperature-measuring resistor 80 is disposed to extend along only one peripheral side of the heat-generating resistor 71. Alternatively, the gas detection element may have another configuration. Specifically, as shown in FIG. 11, a second gas detection element 160 has a configuration such that a temperature-measuring resistor 180 is disposed to extend along three peripheral sides of a heat-generating resistor 171. When the temperature-measuring resistor 180 is disposed in such a manner, the temperature measurement accuracy of the temperature-measuring resistor 180 can be improved.

The second gas detection element 160 includes an electrode 185, a ground electrode 186, an electrode 188, and a ground electrode 189, which are collectively disposed on one of the four sides of the second gas detection element 160. That is, these electrodes are connected to the corresponding members on one of the four sides of the gas detection element. This configuration can simplify the connection between the second gas detection element 160 and other components, as compared with a configuration in which the respective electrodes are disposed away from one another.

In the second gas detection element 160, the electrode 185 is connected to one end of the heat-generating resistor 171 via a wiring film 811 and a wiring line 813, and the ground electrode 186 is connected to the other end of the heat-generating resistor 171 via a wiring film 812 and a wiring line 814. The electrode 188 is connected to one end of the temperature-measuring resistor 180, and the ground electrode 189 is connected to the other end of the temperature-measuring resistor 180.

Figure 12:
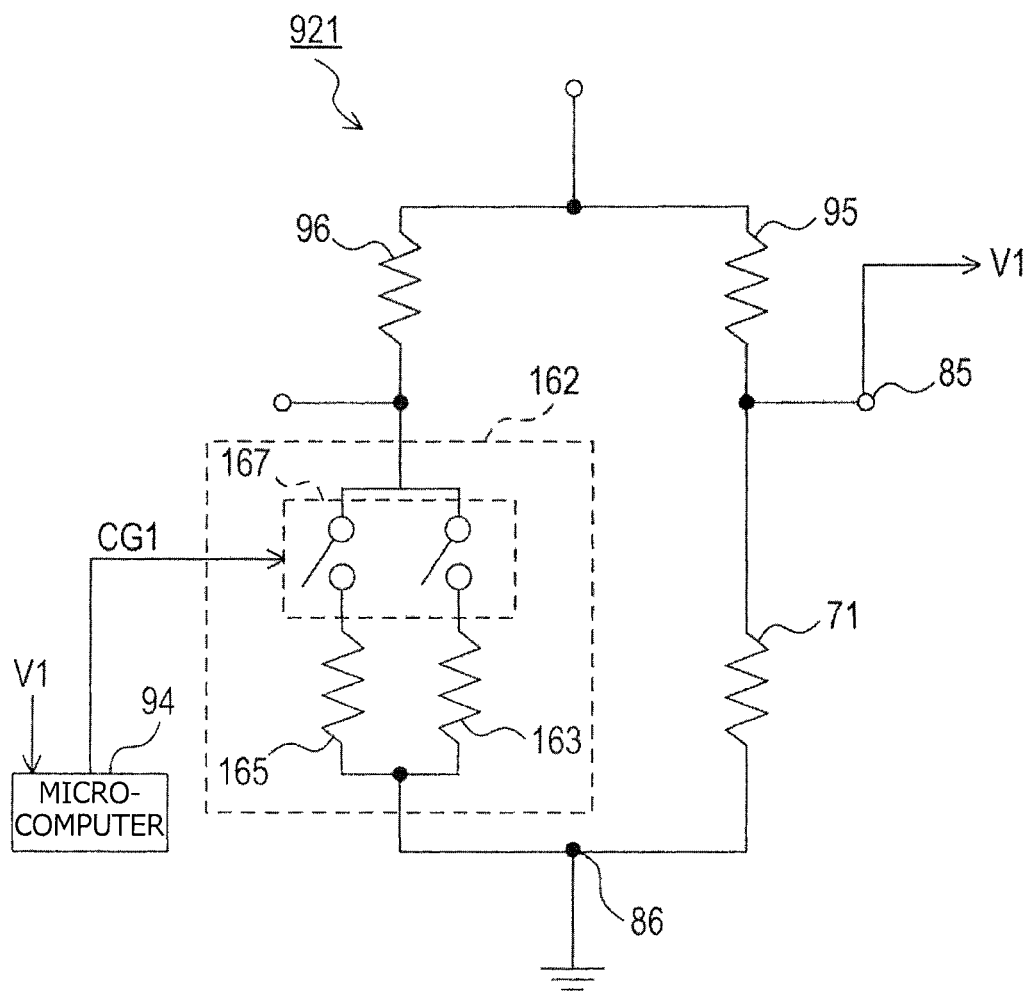
FIG. 12 is a view for describing the configuration of a second Wheatstone bridge circuit 921.

The configuration of the Wheatstone bridge 911 of the gas detection circuit 91 is not limited to that described above. Alternatively, the Wheatstone bridge may have a variable resistor unit. For example, a second Wheatstone bridge circuit 921 shown in FIG. 12 includes the heat-generating resistor 71, the two fixed resistors 95 and 96, and a variable resistor unit 162 capable of changing resistance. That is, the variable resistor unit 162 of the second Wheatstone bridge circuit 921 is substituted for the fixed resistor 97 of the Wheatstone bridge 911.

The variable resistor unit 162 is adapted to change resistance to change the balance of the second Wheatstone bridge circuit 921. The variable resistor unit 162 includes a first fixed resistor 163 and a second fixed resistor 165 having different resistances, and a switch 167 for activating either one of the first fixed resistor 163 and the second fixed resistor 165. The switch 167 is operated by a switching signal CG1 output from the microcomputer 94.

The first fixed resistor 163 has such a resistance that the temperature of the heat-generating resistor 71 reaches a first specific temperature CH (a higher temperature, for example, 400° C.). The second fixed resistor 165 has such a resistance that the temperature of the heat-generating resistor 71 reaches a second specific temperature CL (a lower temperature, for example, 300° C.), which is lower than the first specific temperature CH.

In the gas detection circuit including the second Wheatstone bridge circuit 921, when the temperature of the heat-generating resistor 71 is determined at the first specific temperature CH with the variable resistor unit 162, a voltage at high temperature VH is output as an output value V1, whereas when the temperature of the heat-generating resistor 71 is determined at the second specific temperature CL with the variable resistor unit 162, a voltage at low temperature VL is output as the output value V1.

The microcomputer 94 executes a process of computing the concentration of a flammable gas on the basis of the voltage at high temperature VH and voltage at low temperature VL output from the gas detection circuit, and the output value (temperature-related voltage) from the temperature-measuring circuit 93. Specifically, the ratio of the voltage at high temperature VH to the voltage at low temperature VL (i.e., voltage ratio VC) is firstly computed, and the humidity of an atmosphere is computed on the basis of, for example, the voltage ratio VC, the temperature-related voltage, and specific mapping data. Subsequently, the concentration of a standard gas is computed on the basis of, for example, the voltage at high temperature VH and specific mapping data, and then the concentration of the standard gas is corrected so as to reduce the effects of the temperature and humidity of the atmosphere, to thereby compute the concentration of the flammable gas. Thus, the humidity of the atmosphere is computed on the basis of the ratio of the voltage at high temperature VH to the voltage at low temperature VL (the voltage ratio VC), and the gas concentration is corrected so as to reduce the effect of the humidity of the atmosphere. Therefore, the flammable gas can be detected with high accuracy. The process of computing the concentration of a flammable gas is not limited to that mentioned above (i.e., process utilizing the voltage at high temperature VH and the voltage at low temperature VL), and publicly known computation means may be used as appropriate.

In the aforementioned embodiments, the protection layer 64 is formed of an oxide film mainly containing tantalum oxide. However, the present invention is not limited to this configuration, and the protection layer 64 may be formed of an oxide film mainly containing another tantalum compound. Alternatively, the protection layer 64 may be formed of an oxide film mainly containing niobium oxide ($Nb_2O_5$) or hafnium oxide ($HfO_2$).

The protection layer 64 does not necessarily have a thickness of 15 [nm], but may have a thickness falling within a range of 5 to 200 [nm]. The protection layer 64 may have a thickness equal to or greater than one-fiftieth of that of the heat-generating resistor 71.

The gas detector described above in the embodiments is used for detecting hydrogen gas. The present invention is not limited to such a gas detector, and may be applied to a gas detector for detecting a flammable gas other than hydrogen gas.

DESCRIPTION OF REFERENCE NUMERALS

1: gas detector; 20: element case; 39: detection space; 40: housing case; 41: circuit board; 42: case body; 50, 51: heat-generating element; 60: gas detection element; 61: semiconductor substrate of silicon; 64: protection layer; 66: lower insulation layer; 67: upper insulation layer; 68: insulation layer; 69: insulation protection layer; 71: heat-generating resistor; 80: temperature-measuring resistor; 85: electrode; 86: ground electrode; 88: electrode; 89: ground electrode; 90: control circuit; 94: microcomputer; 160: second gas detection element; 171: heat-generating resistor; 180: temperature-measuring resistor; 185: electrode; 186: ground electrode; 188: electrode; and 189: ground electrode.

The invention claimed is:

1. A gas detector comprising:
   a gas detection element configured such that at least a heat-generating resistor and an insulation layer are laminated on a semiconductor substrate, and the insulation layer covers the heat-generating resistor; and
   a controller that controls energization of the heat-generating resistor and detects a target gas on the basis of resistance of the energized heat-generating resistor, wherein
   the gas detection element has a gas impermeable oxide film laminated on a surface of the insulation layer in such a manner as to cover the insulation layer,
   the oxide film contains at least one of Ta, Nb, and Hf, and forms an outermost surface layer which comes into contact with a gaseous atmosphere containing the target gas,
   an adhesion-enhancing film is formed between the heat-generating resistor and the insulation layer, and
   the insulation layer is made of a material different from a material of the oxide film.

2. The gas detector according to claim 1, wherein the oxide film mainly contains tantalum oxide.

3. The gas detector according to claim 1, wherein the insulation layer has a surface layer formed of silicon nitride.

4. The gas detector according to any one of claims 1 to 3, wherein the oxide film has a thickness equal to or greater than one-fiftieth of a thickness of the heat-generating resistor as measured in a direction perpendicular to front and back surfaces of the semiconductor substrate.

5. The gas detector according to any one of claims 1 to 3, wherein the oxide film has a thickness of 5 to 200 nm.

6. The gas detector according to claim 4, wherein the thickness of the oxide film is a distance between the surface of the insulation layer and a surface of the oxide film which comes into contact with the gaseous atmosphere.

7. The gas detector according to claim 1 or 2, wherein the oxide film is formed through a sputtering process.

8. The gas detector according to claim 1 or 2, wherein the target gas is hydrogen gas.

9. The gas detector according to claim 1 or 2, which is configured such that at least the gas detection element is disposed at a specific position on a fuel cell system that generates electricity from hydrogen and oxygen, and is adapted to detect hydrogen gas used in the fuel cell system.

10. The gas detector according to claim 2, wherein the insulation layer has a surface layer formed of silicon nitride.

11. The gas detector according to claim 5, wherein the thickness of the oxide film is a distance between the surface of the insulation layer and a surface of the oxide film which comes into contact with the gaseous atmosphere.

12. The gas detector according to claim 1, wherein the adhesion-enhancing film is made of tantalum.

13. The gas detector according to claim 1, further comprising a platinum film formed on the adhesion-enhancing film, wherein the adhesion-enhancing film is provided to enhance the adhesion between the platinum film and the insulation layer.

14. The gas detector according to claim 1, wherein the insulation layer is made of either silicon dioxide or silicon nitride.

* * * * *